US012740964B2

(12) United States Patent
Lin et al.

(10) Patent No.: US 12,740,964 B2
(45) Date of Patent: Sep. 22, 2026

(54) USE OF PHTHALIDE COMPOUNDS IN TREATMENT OF MENINGIOMA

(71) Applicant: EVERFRONT BIOTECH INC., New Taipei City (TW)

(72) Inventors: Shinn-Zong Lin, New Taipei City (TW); Tsung-Lang Chiu, New Taipei City (TW); Horng-Jyh Harn, New Taipei City (TW); Tzyy-Wen Chiou, New Taipei City (TW); Jui-Hao Lee, New Taipei City (TW)

(73) Assignee: EVERFRONT BIOTECH INC., New Taipei City (TW)

( * ) Notice: Subject to any disclaimer, the term of this patent is extended or adjusted under 35 U.S.C. 154(b) by 589 days.

(21) Appl. No.: 18/270,071

(22) PCT Filed: Dec. 29, 2021

(86) PCT No.: PCT/CN2021/142454

§ 371 (c)(1),
(2) Date: Jun. 28, 2023

(87) PCT Pub. No.: WO2022/143766

PCT Pub. Date: Jul. 7, 2022

(65) Prior Publication Data

US 2024/0082205 A1 Mar. 14, 2024

Related U.S. Application Data

(60) Provisional application No. 63/131,638, filed on Dec. 29, 2020.

(51) Int. Cl.

| | |
|---|---|
| ***A61K 31/343*** | (2006.01) |
| ***A61K 9/00*** | (2006.01) |
| ***A61K 31/17*** | (2006.01) |
| ***A61K 31/192*** | (2006.01) |
| ***A61K 31/222*** | (2006.01) |
| ***A61K 31/235*** | (2006.01) |
| ***A61K 31/4164*** | (2006.01) |
| ***A61K 31/513*** | (2006.01) |
| ***A61K 31/7068*** | (2006.01) |
| ***A61K 45/06*** | (2006.01) |
| ***A61P 35/00*** | (2006.01) |

(52) U.S. Cl.

CPC .......... *A61K 31/343* (2013.01); *A61K 9/0019* (2013.01); *A61K 9/0024* (2013.01); *A61K 31/17* (2013.01); *A61K 31/192* (2013.01); *A61K 31/222* (2013.01); *A61K 31/235* (2013.01); *A61K 31/4164* (2013.01); *A61K 31/513* (2013.01); *A61K 31/7068* (2013.01); *A61K 45/06* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 9,018,251 | B2 * | 4/2015 | Harn ....................... | A61P 35/00 514/473 |
| 2012/0178803 | A1 | 7/2012 | Harn et al. | |
| 2016/0324826 | A1 | 11/2016 | Lin et al. | |
| 2018/0311208 | A1 | 11/2018 | Harn et al. | |

FOREIGN PATENT DOCUMENTS

| | | | |
|---|---|---|---|
| CN | 1943606 | A | 4/2007 |
| CN | 104042606 | A | 9/2014 |
| CN | 106466315 | A | 3/2017 |

OTHER PUBLICATIONS

Huntoon et. al. ((2020), Meningioma: A Review of Clinicopathological and Molecular Aspects, Frontiers in Oncology, 10, 1-14) (Year: 2020).*

English translation of: You Yongping, et al: "Telomerase Activity and Regulation in Meningiomas", Chinese Journal of Neurosurgery, vol. 20, No. 1, Jan. 31, 2004 (Jan. 31, 2004), pp. 26-29, XP055948241, ISSN: 1001-2346 (pp. 1-9).

International search report PCT/CN2021/142454 dated Apr. 1, 2022 (pp. 1-4).

Guo Chengcheng, et al.: "Medical Treatment of Meningioma", Guangdong Yixue—Guangdong Medical Journal, Guangdong Sheng Yixue Qingbao Yanjiusuo, Guangzhou, CN, vol. 38, No. 24, Dec. 31, 2017 (Dec. 31, 2017), CN pp. 3720-3722, XP055948239, ISSN: 1001-9448, DOI: 10.13820/j.cnki.gdyx.20171225.018 (with English abstract).

You Yongping, et al.: "Telomerase Activity and Regulation in Meningiomas", Chinese Journal of Neurosurgery, vol. 20, No. 1, Jan. 31, 2004 (Jan. 31, 2004), pp. 26-29, XP055948241, ISSN: 1001-2346.

Yen, S. Y. et al.: "Biodegradable interstitial release polymer loading a novel small molecule targeting Axl receptor tyrosine kinase and reducing brain tumour migration and invasion.", Oncogene, vol. 35, No. 17, Aug. 10, 2015 (Aug. 10, 2015), pp. 2156-2165, XP055441896, ISSN: 0950-9232, DOI: 10.1038/onc.2015.277.

Alan A. Moazzam et al., Recent developments in chemotherapy for meningiomas: a review. Journal of Neurosurgery. (Neurosurg Focus) 2013; 35: 1-10. (http://thejns.org/doi/abs/10.3171/2013.10.FOCUS13341).

(Continued)

*Primary Examiner* — Juliet C Switzer
*Assistant Examiner* — Dawanna Shar-Day White
(74) *Attorney, Agent, or Firm* — Millen, White, Zelano and Branigan, P.C.; Jennifer L. King

(57) ABSTRACT

The present invention relates to the use of compounds of formula (I) and formula (II) and/or pharmaceutically acceptable salts of the aforementioned compounds in the treatment of meningioma and the reduction of the recurrence rate of meningioma. In formulas (I) and (II), R1 is C1-C20 alkyl, C3-C10 cycloalkyl, C6-C20 aryl, C1-C20 alkoxy, C6-C20 aryloxy, or halogen; p is 0 to 3; R2 is H, C1-C20 alkyl, or C6-C20 aryl; and R3 is H, C1-C20 alkyl, C3-C10 cycloalkyl, or C6-C20 aryl.

18 Claims, 3 Drawing Sheets

(56) References Cited

OTHER PUBLICATIONS

Salvatore Papa et al., The ERK and JNK pathways in the regulation of metabolic reprogramming. Oncogene. 2019; 38: 2223-2240. https://doi.org/10.1038/s41388-018-0582-8.
Shripad V. Bhagwat et al., ERK Inhibitor LY3214996 Targets ERK Pathway-Driven Cancers: A Therapeutic Approach Toward Precision Medicine, Mol Cancer Ther. Feb. 2020; 19(2):325-336. doi: 10.1158/1535-7163.MCT-19-0183.
Masashi Okada et al., The novel JNK inhibitor AS602801 inhibits cancer stem cells in vitro and in vivo, Oncotarget. May 10, 2016;7(19):27021-32.
Mesfin Fassil B. et al: "Gliomas", StatPearls, NCBI Bookshelf, Aug. 12, 2024, pp. 1-11. URL: https://www.ncbi.nlm.nih.gov/books/NBK441874/.
Huang Yu-Fen et al: "Genetic mutation patterns among glioblastoma patients in the Taiwanese population—insights from a single institution retrospective study", Cancer Gene Therapy, Feb. 28, 2024, vol. 31, pp. 894-903.
Moazzam Alan A. MD. et al: "Recent developments in chemotherapy for meningiomas: a review", Neurosurgery Focus, Dec. 2013, vol. 35, Iss. 6, pp. 1-10.
Gong Wenxia et al: "Neuroprotective and Cytotoxic Phthalides from Angelicae Sinensis Radix", Molecules, Apr. 26, 2016, vol. 21, No. 5, Article 549, pp. 1-11.
Ferrantini Maria et al: "Interferon-a and cancer: Mechanisms of action and new perspectives of clinical use", Biochimie, 2007, vol. 89, Iss. 6-7, pp. 884-893.
Scarpignato Carmelo et al: "Somatostatin Analogs for Cancer Treatment and Diagnosis: An Overview", Chemotherapy, Mar. 12, 2001, vol. 47, Suppl. 2, pp. 1-29.
Meadows Kellen L. et al: "Anti-VEGF Therapies in the Clinic", Cold Spring Harbor Perspectives in Medicine, Oct. 1, 2012, vol. 2, No. 10, a006577, pp. 1-27.
Anonymous, "Monoclonal antibody therapy", Wikipedia, 1 page. URL: https://en.wikipedia.org/wiki/Monoclonal_antibody_therapy ; retrieved Apr. 2, 2026.
Anonymous, "Proton Therapy", Johns Hopkins Medicine, 3 pages. URL: https://www.hopkinsmedicine.org/health/treatment-tests-and-therapies/proton-therapy ; retrieved Feb. 9, 2026.
Anonymous, "Lutathera Infusion Treatment", Rutgers Cancer Institute, 1 page. URL: https://cinj.org/patient-care/lutathera-infusion-treatment ; retrieved Mar. 2, 2026.
Fonkem Ekokobe et al: "NovoTTF-100A: a new treatment modality forrecurrent glioblastoma", Expert Review of Neurotherapeutics, Abstract, Aug. 2012, vol. 12, No. 8, 1 page.
Yust-Katz Shlomit et al: "A phase II, open-label, single-arm trial of pembrolizumab for refractory atypical and anaplastic meningioma and hemangiopericytoma.", Journal of Clinical Oncology, Abstract, May 28, 2021, vol. 39, No. 15, 2 pages.

* cited by examiner

USE OF PHTHALIDE COMPOUNDS IN TREATMENT OF MENINGIOMA

FIELD

The present invention relates to the field of meningioma treatment. And specifically, the present invention relates to the uses of a compound of formula (I), a compound of formula (II), and/or pharmaceutically acceptable salts thereof in treating meningiomas and reducing meningioma recurrence rate.

BACKGROUND

Meningiomas derive from a location between the brain and skull or between the spinal cord and spine. According to the World Health Organization (WHO) classification, meningiomas can be classified into three grades: grade I benign meningiomas, grade II atypical meningiomas, and grade III malignant meningiomas. Among all meningiomas, benign meningiomas are about 90%, while atypical and malignant meningiomas are about 10%. Although the proportion of atypical meningiomas and malignant meningiomas is low, they are clinically focused due to their high lethal rate, poor prognosis and no available medicine.

Currently, no chemical drugs in clinical practice can effectively treat meningiomas. Therefore, the therapies for treating meningiomas still mainly rely on surgery and radiotherapy. However, not all meningioma patients can be treated with surgery based on the consideration of surgical risks (such as the location of the tumor, age and body condition of the patient, etc.). Even for patients who can undergo surgery, their normal brain tissue may be damaged during the surgery, or they may experience many side effects after surgery, such as cerebral edema, cramps, body weakness, abnormal coordination, personality change, disorders of language and thinking, and even death, etc. As for patients who are treated with radiotherapy, they often experience side effects such as skin rubeosis and stabbing pain, hair loss, fatigue, nausea and vomiting, headache, memory loss, tetany, etc.

With the research and development of cancer treatment, targeted therapy has also begun to be tested in clinics for meningioma patients in recent years. The side effect(s) of targeted therapy is relatively mild, but the complexity of the meningioma microenvironment makes the therapeutic effect(s) of single targeted therapy unclear. For example, a targeted medicine, rapamycin, will inhibit mTOR to simultaneously regulate the activation of multiple proteins to treat meningiomas, similar to the effect of multiple targeted inhibitory drugs.

Therefore, there is a necessity and urgency for continuously developing effective methods or drugs in treating meningiomas and/or reducing meningioma recurrence rate.

SUMMARY

Inventors of the present invention found that the compounds of formula (I) and formula (II) of the present invention and their pharmaceutically acceptable salts are effective in killing meningioma cells and inhibiting meningioma growth and thus can be used to treat meningiomas and/or reduce meningioma recurrence rate.

Therefore, an objective of the present invention is to provide a method for treating meningiomas, comprising administering to a subject in need thereof an effective amount of an active ingredient, wherein the active ingredient is selected from a group consisting of a compound of formula (I), a pharmaceutically acceptable salt of the compound of formula (I), a compound of formula (II), a pharmaceutically acceptable salt of the compound of formula (II), and combinations thereof, (I)

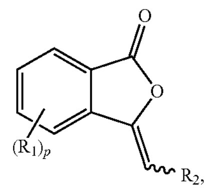

wherein, $R_1$ is C1-C20 alkyl, C3-C10 cycloalkyl, C6-C20 aryl, C1-C20 alkoxy, C6-C20 aryloxy, or halogen;

p is 0 to 3; and $R_2$ is H, C1-C20 alkyl, or C6-C20 aryl, (II)

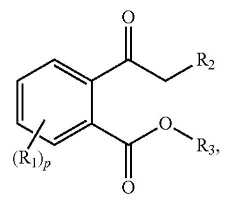

wherein, $R_1$ is C1-C20 alkyl, C3-C10 cycloalkyl, C6-C20 aryl, C1-C20 alkoxy, C6-C20 aryloxy, or halogen;

p is 0 to 3;

$R_2$ is H, C1-C20 alkyl, or C6-C20 aryl; and $R_3$ is H, C1-C20 alkyl, C3-C10 cycloalkyl, or C6-C20 aryl.

In some embodiments of the method for treating meningiomas, according to the present invention, the active ingredient is administered to the subject in an amount that is sufficient to kill meningioma cells and/or inhibit meningioma growth. Preferably, the active ingredient is administered to the subject in an amount that is sufficient to kill meningioma cells and inhibit meningioma growth.

In some embodiments of the method for treating meningiomas according to the present invention, the method further comprises giving the subject a therapy selected from the following group: chemotherapy, radiotherapy, surgery, targeted therapy, hormone therapy, and combinations thereof. Preferably, the method further comprises giving the subject a therapy selected from the following group: chemotherapy, radiotherapy, surgery, and combinations thereof. Wherein, the chemotherapy preferably comprises using an alkylating agent and/or an antimetabolite and, more preferably, comprises using an alkylating agent.

In some embodiments of the method for treating meningiomas according to the present invention, the method further comprises giving the subject a chemotherapy, wherein the chemotherapy comprises using an alkylating agent and/or an antimetabolite, and the alkylating agent and/or the antimetabolite is administered with the active ingredient simultaneously or separately.

Another objective of the present invention is to provide a method for reducing meningioma recurrence rate, comprising administering to a subject in need thereof an effective amount of an active ingredient, wherein the active ingredient is selected from a group consisting of a compound of formula (I), a pharmaceutically acceptable salt of the compound of formula (I), a compound of formula (II), a pharmaceutically acceptable salt of the compound of formula (II), and combinations thereof, (I)

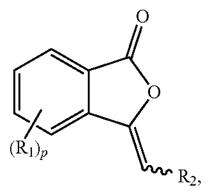

wherein, $R_1$ is C1-C20 alkyl, C3-C10 cycloalkyl, C6-C20 aryl, C1-C20 alkoxy, C6-C20 aryloxy, or halogen;

p is 0 to 3; and $R_2$ is H, C1-C20 alkyl, or C6-C20 aryl, (II)

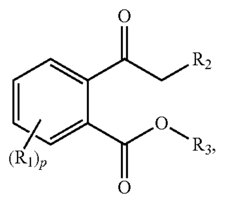

wherein, $R_1$ is C1-C20 alkyl, C3-C10 cycloalkyl, C6-C20 aryl, C1-C20 alkoxy, C6-C20 aryloxy, or halogen;

p is 0 to 3;

$R_2$ is H, C1-C20 alkyl, or C6-C20 aryl; and $R_3$ is H, C1-C20 alkyl, C3-C10 cycloalkyl, or C6-C20 aryl.

In some embodiments of the method for reducing meningioma recurrence rate according to the present invention, the active ingredient is administered to the subject in an amount that is sufficient to inhibit meningioma growth.

In some embodiments of the method for reducing meningioma recurrence rate according to the present invention, the subject has finished a therapy selected from the following group: chemotherapy, radiotherapy, surgery, targeted therapy, hormone therapy, and combinations thereof. Preferably, the subject has finished a chemotherapy, a radiotherapy, a surgery, or combinations thereof.

In some embodiments of the method for reducing meningioma recurrence rate according to the present invention, the method further comprises giving the subject a chemotherapy. Wherein, the chemotherapy preferably comprises using an alkylating agent.

Preferably, in the method for reducing meningioma recurrence rate according to the present invention, the method further comprises giving the subject a chemotherapy, wherein the chemotherapy comprises using an alkylating agent, and the alkylating agent is administered with the active ingredient simultaneously or separately.

In some embodiments of the methods for treating meningiomas and reducing meningioma recurrence rate according to the present invention, in the compound of formula (I), p is 0, $R_2$ is H, C1-C20 alkyl, or C6-C20 aryl; and in the compound of formula (II), p is 0, $R_2$ is H, C1-C20 alkyl, or C6-C20 aryl, $R_3$ is H, C1-C20 alkyl, C3-C10 cycloalkyl, or C6-C20 aryl. Preferably, in the compound of formula (I), p is 0, $R_2$ is C1-C20 alkyl; and in the compound of formula (II), p is 0, $R_2$ is C1-C20 alkyl, $R_3$ is H. More preferably, in the compound of formula (I), p is 0, $R_2$ is C1-C6 alkyl; and in the compound of formula (II), p is 0, $R_2$ is C1-C6 alkyl, $R_3$ is H.

In some embodiments of the methods for treating meningiomas and reducing meningioma recurrence rate according to the present invention, if the active ingredient is a pharmaceutically acceptable salt of the compound of formula (I) and/or of the compound of formula (II), the pharmaceutically acceptable salt is at least one of a lithium salt, a sodium salt, a potassium salt, a magnesium salt, a calcium salt, and a zinc salt.

In some embodiments of the methods for treating meningiomas and reducing meningioma recurrence rate according to the present invention, the active ingredient is administered to the subject by one or more of the following administration routes: oral administration, intranasal administration, transdermal administration, subcutaneous injection, intramuscular injection, intraperitoneal injection, intravenous injection, subcutaneous implantation, and inter-tissue implantation. Preferably, the active ingredient is administered to the subject by one or more of the following administration routes: oral administration, intramuscular injection, intravenous injection, subcutaneous implantation, and inter-tissue implantation. More preferably, the active ingredient is administered to the subject in a form of a wafer.

Still another objective of the present invention is to provide a pharmaceutical composition for use in treating meningiomas, comprising an active ingredient and a pharmaceutically acceptable carrier, wherein the active ingredient is described above. Preferably, the pharmaceutical composition is used to kill meningioma cells and/or inhibit meningioma growth. More preferably, the pharmaceutical composition is used to kill meningioma cells and inhibit meningioma growth.

In some embodiments of the pharmaceutical composition for use in treating meningiomas according to the present invention, the pharmaceutical composition is used in combination with a therapy selected from the following group: chemotherapy, radiotherapy, surgery, targeted therapy, hormone therapy, and combinations thereof. Preferably, the pharmaceutical composition is used in combination with a chemotherapy, a radiotherapy, and/or a surgery. Wherein, the chemotherapy preferably comprises using an alkylating agent and/or an antimetabolite, and more preferably comprises using an alkylating agent.

In some embodiments of the pharmaceutical composition for use in treating meningiomas according to the present invention, the pharmaceutical composition is used in combination with a chemotherapy, wherein the chemotherapy comprises using an alkylating agent and/or an antimetabolite, and the alkylating agent and/or the antimetabolite is used with the pharmaceutical composition simultaneously or separately.

Still another objective of the present invention is to provide a pharmaceutical composition for use in reducing meningioma recurrence rate, comprising an active ingredient and a pharmaceutically acceptable carrier, wherein the active ingredient is described above. Preferably, the pharmaceutical composition is used to inhibit meningioma growth.

In some embodiments of the pharmaceutical composition for use in reducing meningioma recurrence rate according to the present invention, the pharmaceutical composition is used after finishing a therapy selected from the following group: chemotherapy, radiotherapy, surgery, targeted therapy, hormone therapy, and combinations thereof. Preferably, the pharmaceutical composition is used after finishing a chemotherapy, a radiotherapy, and/or a surgery. Wherein, the chemotherapy preferably comprises using an alkylating agent.

In some embodiments of the pharmaceutical composition for use in reducing meningioma recurrence rate according to the present invention, the pharmaceutical composition is used in combination with a chemotherapy, wherein the chemotherapy comprises using an alkylating agent, and the alkylating agent is used with the pharmaceutical composition simultaneously or separately.

Still another objective of the present invention is to provide use of an active ingredient in the manufacture of a medicament for treating meningiomas and/or reducing meningioma recurrence rate, wherein the active ingredient is described above.

In some embodiments of the use according to the present invention, the medicament is used for treating meningiomas by killing meningioma cells and/or inhibiting meningioma growth. Preferably, the medicament is used for treating meningiomas by killing meningioma cells and inhibiting meningioma growth. In some embodiments of the use according to the present invention, the medicament is used for reducing meningioma recurrence rate by inhibiting meningioma growth.

In some embodiments of the use according to the present invention, the medicament is used in combination with a therapy selected from the following group to treat meningiomas: chemotherapy, radiotherapy, surgery, targeted therapy, hormone therapy, and combinations thereof. Preferably, the medicament is used in combination with a chemotherapy, a radiotherapy, and/or a surgery to treat meningiomas. Wherein, the chemotherapy preferably comprises using an alkylating agent and/or an antimetabolite, and more preferably comprises using an alkylating agent.

In some embodiments of the use according to the present invention, the medicament is used in combination with a chemotherapy to treat meningiomas, and wherein the chemotherapy comprises using an alkylating agent and/or an antimetabolite, and the alkylating agent and/or the antimetabolite is used with the active ingredient simultaneously or separately.

In some embodiments of the use according to the present invention, the medicament is used after finishing a therapy selected from the following group to reduce meningioma recurrence rate: chemotherapy, radiotherapy, surgery, targeted therapy, hormone therapy, and combinations thereof. Preferably, the medicament is used after finishing a chemotherapy, a radiotherapy, and/or a surgery to reduce meningioma recurrence rate. Wherein, the chemotherapy preferably comprises using an alkylating agent.

In some embodiments of the use according to the present invention, the medicament is used in combination with a chemotherapy to reduce meningioma recurrence rate, and wherein the chemotherapy comprises using an alkylating agent, and the alkylating agent is used with the medicament simultaneously or separately.

In the pharmaceutical composition or the use according to the present invention, the pharmaceutical composition and the medicament are present in a form for oral administration, intranasal administration, transdermal administration, subcutaneous injection, intramuscular injection, intraperitoneal injection, intravenous injection, subcutaneous implantation, and inter-tissue implantation. Preferably, the pharmaceutical composition and the medicament are present in a form for oral administration, intramuscular injection, intravenous injection, subcutaneous implantation, or inter-tissue implantation. More preferably, the pharmaceutical composition and the medicament are present in a form of a wafer.

In the method, pharmaceutical composition or use according to the present invention, the meningiomas are at least one of benign meningiomas, atypical meningiomas, and malignant meningiomas.

The detailed technology and some embodiments implemented for the present invention are described in the following for a person having original skills in the art to well appreciate the features of the claimed invention.

DESCRIPTION OF EMBODIMENTS

Figure 1:
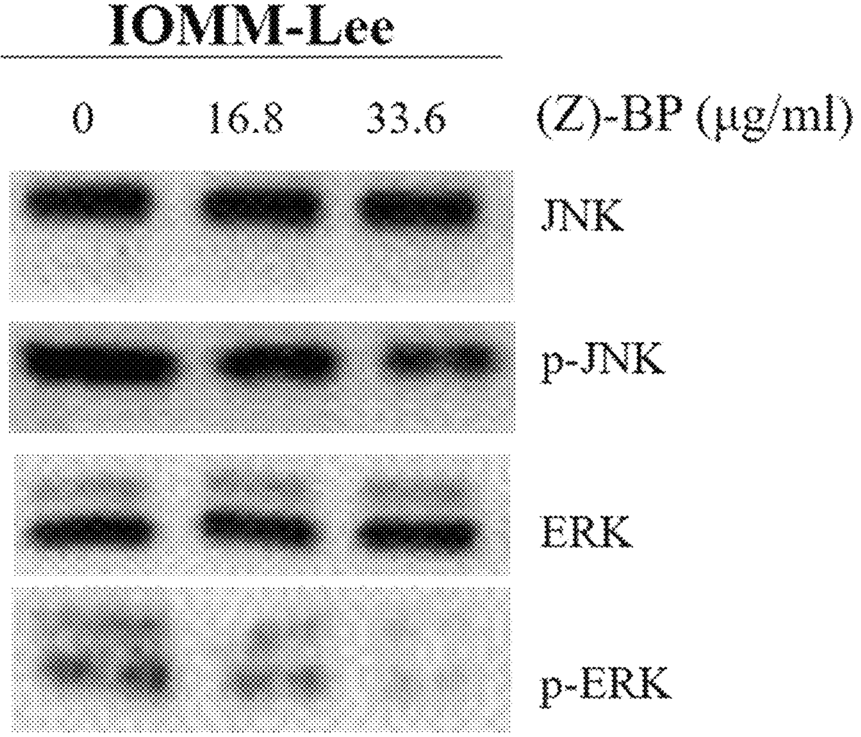
FIG. 1 shows a picture of expressions of ERK protein, JNK protein, p-ERK protein, p-JNK protein, and β-actin in IOMM-Lee cells treated with Z-butylidenephthalide at different concentrations, wherein the expressions were analyzed by Western Blotting.

The detailed techniques and some embodiments of the present invention will be described in the following, so that a person having ordinary art skills in the art can understand the features of the present invention. However, without departing from the spirit of the present invention, the present invention may be embodied in various embodiments and should not be limited to the embodiments described in the specification.

Unless otherwise indicated herein, the words "a," "an," "the," or the like recited in the specification (especially in the claims) should include both the singular and plural forms. The term "an effective amount" refers to the amount of the compound that can at least partially alleviate the condition of a subject when it is administered to the subject (e.g., maintaining or reducing the size of meningiomas). The term "treat," "treating" or "treatment" should not be construed as referring to treat a subject until the subject has completely recovered, but should include maintaining the progression or symptoms of diseases in a substantially static state, increasing the recovery rate of a subject, alleviating the severity of a particular condition (e.g., alleviating the symptoms of cachexia), and increasing the quality of life of a patient. The term "reduce recurrence rate" or "reducing recurrence rate" refers to preventing the recurrence of a particular condition, maintaining a subject's health status after treatment, or prolonging the progression-free survival of a subject. The term "subject" refers to human and non-human mammalians (e.g., dogs, cats).

In this specification, the term "administering (a) and (b) simultaneously" refers to administering (a) and (b) to a subject at the same time. The term "administering (a) and (b) separately" refers to administering (a) and (b) at different time points sequentially, by administering (a) first or administering (b) first, or by administering (a) and (b) independently in a given time interval, such that the subject receives both the administrations of (a) and (b) during the treatment course.

The numerical ranges (e.g., 5 to 100) used herein should be construed as including all of the rational numbers within the ranges and ranges consisting of any rational numbers within the ranges. Therefore, the numerical ranges used herein should include all the possible combinations of numerical values between the listed minimum and maximum values. In addition, the word "about" presented before the values as used herein substantially represents the values that can be increased or decreased in a normal and reasonable amount that a person having ordinary skills in the art considers acceptable. For example, the word "about" presented before the values as used herein substantially represents values within ±10% of the stated value and, more preferably, within ±5%.

Currently, no chemical drugs available in clinical practice can effectively treat meningiomas. For example, temozolomide (TMZ), which is usually used in clinics to treat gliomas, has been proven to be failed for meningioma treatment in phase II clinical trials. The fact described above can be found in such as "Recent developments in chemotherapy for meningiomas: a review. *Journal of Neurosurgery.* 2013; 35: 1-10", which is entirely incorporated hereinto by reference. As described above, other therapies (e.g., surgery, radiotherapy, targeted therapy) also have many problems.

Inventors of the present invention found that the compounds of formula (I) and formula (II) of the present invention, and their pharmaceutically acceptable salts are effective in killing meningioma cells, and have an effect on inhibiting meningioma growth, and thus can be used to treat meningiomas and reduce meningioma recurrence rate. Therefore, the present invention relates to applications of a compound of formula (I), a compound of formula (II), and/or pharmaceutically acceptable salts thereof in treating meningiomas and/or reducing meningioma recurrence rate:

(I)

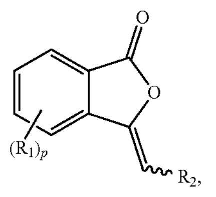

wherein, $R_1$ is C1-C20 alkyl, C3-C10 cycloalkyl, C6-C20 aryl, C1-C20 alkoxy, C6-C20 aryloxy, or halogen;

p is 0 to 3; and $R_2$ is H, C1-C20 alkyl, or C6-C20 aryl, (II)

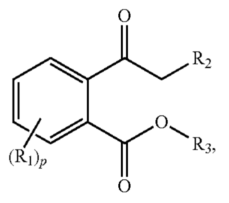

wherein, $R_1$ is C1-C20 alkyl, C3-C10 cycloalkyl, C6-C20 aryl, C1-C20 alkoxy, C6-C20 aryloxy, or halogen;

p is 0 to 3;

$R_2$ is H, C1-C20 alkyl, or C6-C20 aryl; and $R_3$ is H, C1-C20 alkyl, C3-C10 cycloalkyl, or C6-C20 aryl.

The above applications include: a method for treating meningiomas and/or reducing meningioma recurrence rate, comprising administering to a subject in need thereof an effective amount of an active ingredient; a pharmaceutical composition for use in treating meningiomas and/or reducing meningioma recurrence rate, comprising an active ingredient and a pharmaceutically acceptable carrier; and use of an active ingredient in the manufacture of a medicament for treating meningiomas and/or reducing meningioma recurrence rate. The aforesaid active ingredient is selected from a group consisting of a compound of formula (I), a pharmaceutically acceptable salt of the compound of formula (I), a compound of formula (II), a pharmaceutically acceptable salt of the compound of formula (II), and combinations thereof.

In the applications according to the present invention, the meningiomas are at least one of benign meningiomas, atypical meningiomas, and malignant meningiomas. In some embodiments of the present invention, the meningiomas are benign meningiomas or malignant meningiomas.

In the applications according to the present invention, preferably, in the compound of formula (I), p is 0, $R_2$ is H, C1-C20 alkyl, or C6-C20 aryl; and in the compound of formula (II), p is 0, $R_2$ is H, C1-C20 alkyl, or C6-C20 aryl, $R_3$ is H, C1-C20 alkyl, C3-C10 cycloalkyl, or C6-C20 aryl. More preferably, in the compound of formula (I), p is 0, $R_2$ is C1-C20 alkyl; and in the compound of formula (II), p is 0, $R_2$ is C1-C20 alkyl, $R_3$ is H. In some embodiments of the present invention, the compound of formula (I) is Z-butylidenephthalide or E-butylidenephthalide. In some embodiments of the present invention, the compound of formula (II) is 2-pentanolybenzoic acid.

In the applications according to the present invention, the pharmaceutically acceptable salt of compounds of formula (I) and formula (II) is at least one of a lithium salt, a sodium salt, a potassium salt, a magnesium salt, a calcium salt, and a zinc salt. In some embodiments of the present invention, the pharmaceutically acceptable salt of compounds of formula (I) and formula (II) is a sodium salt, such as sodium 2-pentanoylbenzoate.

In the applications according to the present invention, the compounds of formula (I) and formula (II) and their pharmaceutically acceptable salts can be commercially available or be prepared by a synthesis method known in the art of the present invention.

In the applications according to the present invention, the alkylating agent can be nitrogen mustards, ethylenimine, sulfonate ester and polyol, nitrosoureas, hydrazine, triazine or platinum. Examples of the alkylating agent suitable for the present invention include, but are not limited to, dacarbazine (DTIC), chlorambucil, chlormethine hydrochloride, temozolomide, MTIC (monomethyl triazeno imidazole carboxamide; i.e. an anti-cancer active ingredient produced by metabolizing temozolomide), busulfan, cyclophosphamide (CYC), ifosfamide (IFOS), carmustine (BCNU), lomustine (CCNU), streptozocin, cisplatin (CDDP), carboplatin (CBDCA), oxaliplatin, thiotepa, procarbazine (PCZ), melphalan, and combinations thereof.

In the applications according to the present invention, the antimetabolite can be antifolates, pyrimidine antagonists, or purine antagonists. Examples of the antimetabolite suitable for the present invention include but are not limited to, methotrexate (MTX), 6-mercaptopurine (6-MP), 5-fluorouracil (5-FU), cytarabine (Ara-C), floxuridine (FUDR), tegafur, capecitabine, gemcitabine, hydroxyurea, pemetrexed, TS-1 (i.e., a complex medicine containing a prodrug of 5-FU, tegafur), azathioprine (i.e., a prodrug of 6-MP), cladribine, clofarabine, decitabine, fludarabine, nelarabine, pentostatin, pralatrexate, thioguanine, trifluridine/tipiracil combination, and combinations thereof.

In the applications according to the present invention, the active ingredient, pharmaceutical composition or medicament can be administered systemically or topically and can be delivered by various drug delivery systems (DDSs). Suitable drug delivery systems include an oral drug delivery system, a transdermal drug delivery system, an injectable drug delivery system, an inhalation drug delivery system, and a transmucosal drug delivery system, etc. For example, to enhance bioavailability, control drug release speed, target the lesion precisely and reduce side effects, the active ingredient, pharmaceutical composition or medicament of the present invention can be delivered by liposomes, microcapsules, nanoparticles, microneedles, etc., but is not limited thereby.

In the applications according to the present invention, depending on the desired purpose(s), the active ingredient, pharmaceutical composition or medicament can be provided in any suitable form without particular limitations. For example, the active ingredient, pharmaceutical composition or medicament of the present invention can be administered to the subject by one or more of the following administration routes: oral administration, intranasal administration (e.g., spray, nasal drops, etc.), transdermal administration (e.g., patch, ointment, etc.), subcutaneous injection, intramuscular injection, intraperitoneal injection, intravenous injection (including drip infusion and bolus injection), subcutaneous implantation, and inter-tissue implantation (such as a wafer), but is not limited thereby.

In the applications according to the present invention, the active ingredient, pharmaceutical composition or medicament can be administered or used with an alkylating agent and/or an antimetabolite simultaneously or separately. For example, when the active ingredient, pharmaceutical composition or medicament is administered or used with the alkylating agent and/or the antimetabolite simultaneously or separately, the active ingredient, pharmaceutical composition or medicament can be administered to a subject by subcutaneous implantation or inter-tissue implantation or via a drug release dosage form first, and subsequently, the alkylating agent and/or the antimetabolite can be administered to the subject by oral administration or injection in a given time interval.

In the method according to the present invention, the active ingredient is administered to a subject in need in a form of a pharmaceutical composition or a medicament, wherein the pharmaceutical composition or the medicament comprises an active ingredient and a pharmaceutically acceptable carrier or consists of an active ingredient and a pharmaceutically acceptable carrier. Depending on the form and purpose(s), the pharmaceutically acceptable carrier can be those known and adopted in the art, including an excipient, a diluent, an auxiliary, a stabilizer, an absorption enhancer, a disintegrating agent, a hydrotropic agent, an emulsifier, an antioxidant, an adhesive, a binder, a tackifier, a dispersant, a suspending agent, a lubricant, a hygroscopic agent, etc.

As a dosage form for oral administration, the pharmaceutical composition or the medicament provided by the present invention can be provided in a form suitable for oral administration, wherein a liquid form suitable for oral administration includes a syrup, an oral solution, a suspension, an elixir, etc., and a solid form suitable for oral administration includes a powder, a granule, a troche, a dragee, an enteric-coated tablet, a chewable tablet, an effervescent tablet, a film-coated tablet, a capsule, a long-acting slow-release tablet, etc. The pharmaceutical composition or the medicament provided by the present invention can comprise any pharmaceutically acceptable carrier that will not adversely affect the desired effects of the active ingredient (i.e., at least one of the compound of formula (I), the compound of formula (II), and the pharmaceutically acceptable salts thereof as disclosed in the present invention). For example, the pharmaceutically acceptable carrier of the aforesaid liquid form includes, but is not limited to, water, saline, dextrose, glycerol, ethanol or its analogs, oil (e.g., olive oil, castor oil, cottonseed oil, peanut oil, corn oil, and germ oil), glycerin, polyethylene glycol, and combinations thereof. The pharmaceutically acceptable carrier of the aforesaid solid form includes cellulose, starch, kaolinite, bentonite, sodium citrate, gelatin, agar, carboxymethyl cellulose, gum arabic, seaweed gel, glyceryl monostearate, calcium stearate, and combinations thereof.

The dosage form suitable for transdermal administration can also comprise any pharmaceutically acceptable carrier that will not adversely affect the desired effect(s) of the active ingredient (i.e., at least one of the compound od formula (I), the compound of formula (II), and the pharmaceutically acceptable salts thereof), such as water, mineral oil, propylene glycol, polyethylene oxide, liquid petrolatum, sorbitan monosterate, and polysorbate 60. The pharmaceutical composition or the medicament of the present invention can be provided by any suitable method in a dosage form suitable for transdermal administration, such as in the form of an emulsion, a cream, an oil, a gel (such as a hydrogel), a paste (such as a dispersing paste, an ointment), a lotion, a spray, and a patch (such as a microneedle patch), but is not limited thereby.

As the form suitable for injection or drip infusion, the pharmaceutical composition or the medicament can comprise one or more ingredients, such as an isotonic solution, a salt-buffered saline (e.g., phosphate-buffered saline or citrate-buffered saline), a hydrotropic agent, an emulsifier, a 5% sugar solution, and other carriers to provide the pharmaceutical composition or the medicament as an intravenous infusion, an emulsified intravenous infusion, a powder for injection, a suspension for injection, or a powder suspension for injection, etc. Alternatively, the pharmaceutical composition or the medicament can be prepared as a pre-injection solid, and the desired solution for injection is provided by dissolving the pre-injection solid in another solution or suspension or emulsifying it prior to being administered to a subject in need.

As a dosage form suitable for subcutaneous implantation or inter-tissue implantation, the pharmaceutical composition or the medicament provided by the present invention can further comprise one or more ingredients, such as an excipient, a stabilizer, a buffer, and other carriers, to be prepared in a dosage form such as a wafer, a tablet, a pill, a capsule, etc., such that the pharmaceutical composition or the medicament can be implanted into a subject and the active ingredient contained therein (i.e., at least one of the compound od formula (I), the compound of formula (II), and the pharmaceutically acceptable salts thereof) can be slowly and continuously released to the tissue surrounding the administered site to achieve the effects of killing meningioma cells and/or inhibiting meningioma recurrence rate at a locally stable high dose. For example, the pharmaceutical composition or the medicament provided by the present invention can comprise a biocompatible polymer to prepare the pharmaceutical composition or the medicament in a form of a wafer for subcutaneous implantation or inter-tissue implantation, but is not limited thereby. The biocompatible polymer can be commercially available or be prepared by a synthesis method known in the art of the present invention. For example, the biocompatible polymer can be a polyanhydride (such as "p(CPP-SA) copolymer") prepared from bis (p-carboxylphenoxy) propane and sebacic acid.

As for the pharmaceutical composition or the medicament for intranasal administration, the pharmaceutical composition or the medicament can be optionally aerosolized by any suitable approach to facilitate the entry of the active ingredient into the respiratory tract. For example, the pharmaceutical composition or the medicament can be administered through a nebulizer, or a pressurized container (such as a nasal spray), but is not limited thereby. Alternatively, the pharmaceutical composition or the medicament can be prepared as a nasal drop. In addition, the pharmaceutical composition or the medicament provided in accordance with the present invention can further comprise one or more ingredients, such as a penetrant, a surfactant, a viscosity modifier, a pH adjuster, a preservative, a stabilizer, an osmotic pressure regulator, and other carriers, to provide the pharmaceutical composition or the medicament as a dosage form of a nasal spray, a nasal drop, etc.

Optionally, the pharmaceutical composition or the medicament provided in accordance with the present invention can also comprise a suitable amount of an additive, for example, a toner, a coloring agent and the like for enhancing the feeling of using the pharmaceutical composition or the medicament, and a buffer, a conservative, a preservative, an antibacterial agent, an antifungal agent and the like for improving the stability and storability of the pharmaceutical composition or the medicament.

The pharmaceutical composition or the medicament provided in accordance with the present invention can optionally comprise one or more other active ingredients to further enhance the effect of the composition or the medicament or to increase the application flexibility and adaptability of the preparation thus provided, as long as the other active ingredient(s) does not adversely affect the desired effect(s) of the active ingredient (i.e., at least one of the compound of formula (I), the compound of formula (II), and the pharmaceutically acceptable salts thereof).

The pharmaceutical composition or the medicament provided in accordance with the present invention contains at least about 0.0001, 0.0002, 0.0003, 0.0004, 0.0005, 0.001, 0.0015, 0.002, 0.0025, 0.003, 0.0035, 0.004, 0.0045, 0.005, 0.0055, 0.006, 0.0065, 0.007, 0.0075, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 5, 10, 15, 20, 25, 30, 35, 40, 45, 50, 55, 60, 65, 70, 75, 80, 85, 90, 95 or 100 wt % of the active ingredient based on the total weight of the pharmaceutical composition or the medicament, and useful ranges may be selected from any two of these values, for example, about 0.0001 wt % to about 90 wt %, about 0.001 wt % to about 25 wt %, about 0.01 wt % to about 10 wt %, about 0.01 wt % to about 5 wt %, about 0.05 wt % to about 1 wt %, and about 0.05 wt % to about 0.5 wt %.

Depending on the need, age, body weight and health conditions of the subject and the purpose of the application, the pharmaceutical composition or the medicament provided in accordance with the present invention can be taken at various frequencies, such as once a day, multiple times a day, or once every few days, etc. The amount of the active ingredient (i.e., at least one of the compound of formula (I), the compound of formula (II), and the pharmaceutically acceptable salts thereof) in the pharmaceutical composition or the medicament can also be adjusted, for example, to the amount that it should be taken or external used daily, depending on the need in the practical application.

The present invention will be further illustrated in detail with the following specific examples. However, these examples are provided only for illustrating the present invention, and the scope of the present invention is not limited thereby. The scope of the present invention will be indicated in the appended claims.

EXAMPLES

In the following Examples, the used materials and equipment are described as below:

1. Human meningioma cell lines: IOMM-Lee cells (purchased from ATCC; CRL-3370;

belonging to grade III malignant meningioma cells), AMGI-0102 primary culture cells (obtained by the approval according to the human subject research of Hualien Tzu Chi Hospital (Buddhist Tzu Chi Medical Foundation); belonging to grade I benign meningioma cells).

2. Medium for IOMM-Lee cells: RPMI 1640 medium (RPMI 1640, 1×, with 2.05 mM L-Glutamine; purchased from HyClone; product number: SH30027.02) containing 15% Fetal Bovine Serum (FBS; purchased from Gibco; product number: 1939760), 1% penicillin/streptomycin (P/S; purchased from Simply; product number: CC502-0100).
3. Medium for AMGI-0102 cells: DMEM/F12 medium (Dulbecco's Modified Eagle Medium/F12 with L-glutamine, HEPES; purchased from HyClone; product number: SH30023.02) containing 10% Fetal Bovine Serum and 1% penicillin/streptomycin.
4. Z-butylidenephthalide (Z-BP): provided by Everfront Biotech Inc.; purity 99.8%.
5. E-butylidenephthalide (E-BP): provided by Everfront Biotech Inc.; purity 98.01%.
6. 2-pentanolybenzoic acid (BP-OH): provided by Everfront Biotech Inc.; purity 99.6%.
7. Sodium$^2$-pentanoylbenzoate (BPONa): provided by Everfront Biotech Inc.; purity 99.7%.
8. 5-fluorouracil (5-FU): purchased from Sigma; product number: F6627.
9. Carmustine (BCNU): purchased from Sigma; product number: SI-00400-100MG.
10. MTIC: purchased from Biosynth Carbosynth; product number: FM26098.
11. MTT (Thiazolyl Blue tetrazolium bromide, 3-[4,5-dimethylthiahiazo-2-yl]-2,4-dipheny-tetrazolium bromide): purchased from ALFA Aesar™; product number: L11939-000000-16AF.
12. ELISA reader: purchased from Thermo Fisher Scientific; model number: 22662.
13. Antibodies for Western Blotting (1) PhosphoPlus® SAPK/JNK (Thr183/Tyr185) antibody: purchased from Cell Signaling Technology; product number: #8206;

(2) anti-ERK antibody: purchased from Cell Signaling Technology; product number: #4695S;

(3) anti-Phospho-p44/42 MAPK (Erk1/2) (Thr202/Tyr204) antibody: purchased from Cell Signaling Technology; product number: #4370S; and (4) anti-β actin antibody: purchased from Sigma; product number: A5441.

Example 1: Effects of the Compounds of the Present Invention on Killing Meningioma Cells IOMM-Lee cells and AMGI-0102 cells were independently seeded in a 96-well plate ($1\times10^4$ cells/well), and the 96-well plate was placed under an environment of 37° C. and 5% $CO_2$ for 24 hours. After that, the cells in the 96-well plate were subjected to the following procedures:

(a) the cells in different wells were cultured with a medium containing Z-butylidenephthalide, E-butylidenephthalide, 2-pentanolybenzoic acid, or sodium[2]-pentanoylbenzoate, and the 96-well plate was placed under an environment of 37° C. and 5% $CO_2$ for 72 hours;

(b) MTT was added into each well (the final concentration is 0.5 mg/ml), and the 96-well plate was placed under an environment of 37° C. and 5% $CO_2$ for 1.5 hours;

(c) the medium of each well was removed, and then dimethyl sulfoxide was added (100 μl/well); and (d) an absorbance value of each well at 595 nm was measured by an ELISA reader.

The cell viability was calculated based on the absorbance values obtained from the above step (d), and the concentrations of Z-butylidenephthalide, E-butylidenephthalide, 2-pentanolybenzoic acid, and sodium[2]-pentanoylbenzoate to achieve 50% lethal rate (i.e., half maximal inhibitory concentration, $IC_{50}$) for each cell line were further calculated. The results are shown in Table 1.

TABLE 1

| $IC_{50}$ (unit: μg/ml) | | |
|---|---|---|
| | IOMM-Lee | AMGI-0102 |
| Z-butylidenephthalide | 33.5 | 94.5 |
| E-butylidenephthalide | 306.4 | — |
| 2-pentanolybenzoic acid | 304.3 | 1286.3 |
| sodium 2-pentanoylbenzoate | 364.9 | — |

The results of Table 1 show that all of Z-butylidenephthalide, E-butylidenephthalide, 2-pentanolybenzoic acid, and sodium 2-pentanoylbenzoate are effective in killing meningioma cells, and thus can be used to treat meningiomas.

Example 2: Effects of the Compounds of the Present Invention in Combination with a Chemotherapy Drug on Killing Meningioma Cells IOMM-Lee cells and AMGI-0102 cells were treated with the method of Example 1, but in step (a), the cells were cultured with a medium containing "Z-butylidenephthalide and carmustine," "Z-butylidenephthalide and MTIC," or "Z-butylidenephthalide and 5-fluorouracil."

The cell viability was calculated based on the obtained absorbance values, and the $IC_{50}$ of the combinations of Z-butylidenephthalide and different anti-cancer drugs for each cell line were further calculated. Finally, a combination index (CI) was calculated by the Equation A, wherein (D)1, (D)2 independently represent the $IC_{50}$ of a drug 1 and drug 2 when using the aforesaid two drugs in combination with each other, and (Dx)1, (Dx)2 independently represent the $IC_{50}$ of a drug 1 and drug 2 when using the aforesaid two drugs alone. If the combination index (CI) is less than 1, the combination of the two drugs is considered to have a synergistic effect. The results are shown in Table 2.

$$CI = \frac{(D)1}{(Dx)1} + \frac{(D)2}{(Dx)2}. \quad \text{Equation A}$$

TABLE 2

CI values of using Z-butylidenephthalide in combination with carmustine, MTIC, and 5-fluorouracil for killing meningioma cells

| cell line | carmustine | MTIC | 5-fluorouracil |
|---|---|---|---|
| IOMM-Lee | 0.39 | 0.17 | 0.21 |
| AMGI-0102 | 0.80 | 0.59 | 0.15 |

The results of Table 2 show that all the CI values of using Z-butylidenephthalide in combination with a chemotherapy drug such as carmustine, MTIC, 5-fluorouracil, etc. are less than 1; that is, there is a synergistic effect on killing meningioma cells by using the compounds of the present invention in combination with a chemotherapy drug.

Example 3: Effects of the Compounds of the Present Invention on Inhibiting Meningioma Growth 3-1. Observation of Protein Expression It is known that the activations (phosphorylation) of ERK (extracellular signal-regulated kinase) protein and JNK (c-Jun N-terminal kinase) protein in the protein kinase family are related to the proliferation of tumor cells. The aforesaid facts can be found in such as: "The ERK and JNK pathways in the regulation of metabolic reprogramming" *Oncogene.* 2019; 38: 2223-2240; "ERK Inhibitor LY3214996 Targets ERK Pathway-Driven Cancers: A Therapeutic Approach Toward Precision Medicine." *Mol Cancer Ther.* 2020 February; 19(2):325-336; and "The novel JNK inhibitor AS602801 inhibits cancer stem cells in vitro and in vivo." *Oncotarget.* 2016 May 10; 7(19):27021-32, which are entirely incorporated hereinto by reference. Therefore, if the activations of ERK protein and JNK protein in tumor cells can be reduced, the meningioma growth will be inhibited.

IOMM-Lee cells were seeded in a 10 cm culture dish ($1\times10^6$ cells/$cm^2$), and the dish was placed under an environment of 37° C. and 5% $CO_2$ for 24 hours. Then, the cells in different dishes were independently cultured with a medium containing Z-butylidenephthalide at concentrations of 0, 16.8 and 33.6 μg/ml. After culturing for 24 hours, the cells were harvested and subjected to a procedure of protein extraction. Finally, the expressions of the inactivated JNK protein and ERK protein, and the activated p-JNK protein and p-ERK protein in the cells were detected by Western Blotting. Wherein, β-actin was used as an internal control. The results are shown in FIG. 1.

As shown in FIG. 1, either the expression of p-JNK protein or p-ERK protein is significantly decreased along with the increment in the concentration of Z-butylidenephthalide. The aforesaid results indicate that the compounds of the present invention (e.g., Z-butylidenephthalide) can reduce the activations of ERK protein and JNK protein, thereby achieving the effect of inhibiting meningioma cell growth and thus can be used to treat meningiomas and reduce meningioma recurrence rate.

3-2. Human Test

In this example, depending on the approval of the Research Ethics Committee Hualien Tzu Chi Hospital (Buddhist Tzu Chi Medical Foundation; SP109-04), meningioma patients were administered with Z-butylidenephthalide to observe the effects of the compounds of the present invention on inhibiting meningioma growth.

Figure 2:
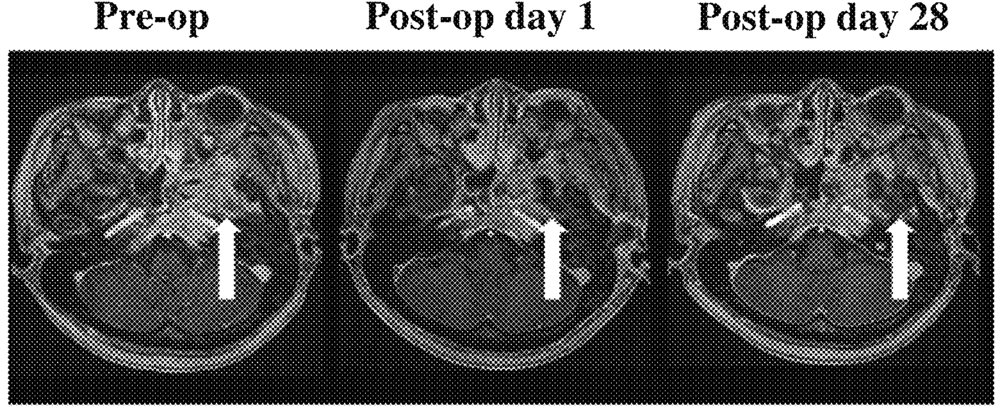
FIG. 2 shows $T_1$-weighted magnetic resonance images ($T_1$-weighted MRI) of the brain for the subject at pre-operation (pre-op) and post-operative (post-op) days 1, 28, 84, 168, and 224.
Figure 2:
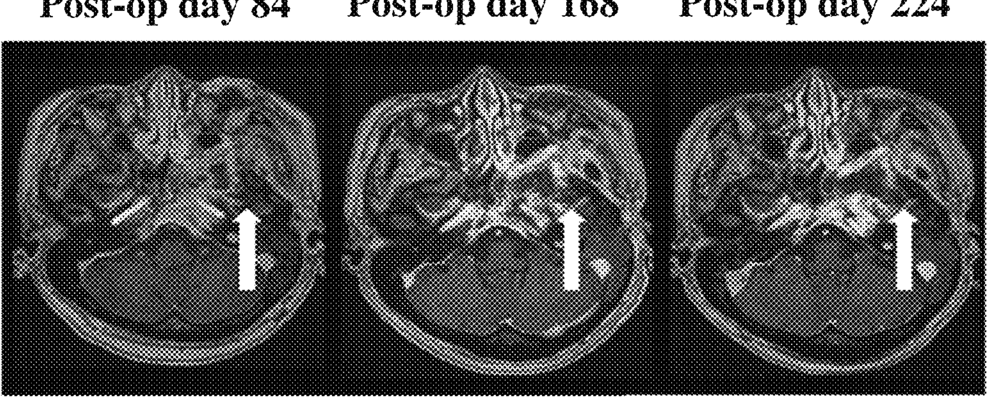

During the surgical operation for resecting meningioma in a subject (suffered with grade III meningioma), six wafers containing Z-butylidenephthalide (75 mg of Z-butylidenephthalide per wafer) were implanted into the cavity generated by resecting meningioma. The subject also took 150 $mg/m^2$ of body surface area/day (the first treatment course) or 200 $mg/m^2$ of body surface area/day (the second to sixth treatment course) of temozolomide via oral administration every day post-operation. The tumor (presented by white arrow) size of the subject was observed at pre-operation, and post-operative days 1, 28, 84, 168, and 224 by $T_1$-weighted magnetic resonance imaging ($T_1$-weighted MRI) using Gadolinium-based contrast agent, and was recorded by taking pictures. The results are shown in FIG. 2. On the other hand, the tumor size in the pictures of the subject's brain (at pre-operation, and post-operative days 1, 28, 84, 168, and 224), obtained by $T_1$-weighted magnetic resonance imaging, was also calculated by using StealthStation S7 software (purchased from Medtronic company, US). The results are shown in FIG. 3.

Figure 3:
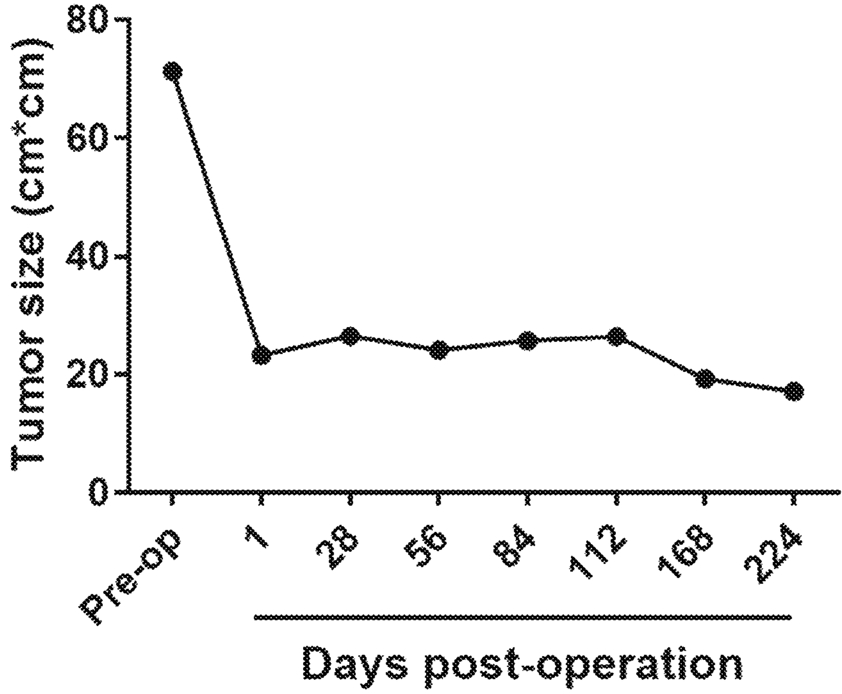
FIG. 3 shows a line chart of tumor size for the subject at pre-operation and post-operative days 1, 28, 56, 84, 112, 168 and 224.

As shown in FIG. 2 and FIG. 3, there is no change in the tumor size of the subject for up to 224 days after the surgical operation. The aforesaid results indicate that the compounds of the present invention are effective in inhibiting meningioma growth, thereby prolonging the progression-free survival of meningiomas, and alleviating the symptoms of cachexia in the meningioma subject. The compounds of the present invention can be used to treat meningiomas and/or reduce meningioma recurrence rate.

What is claimed is:

1. A method for treating meningiomas, comprising administering to a subject in need thereof an effective amount of an active ingredient, wherein the active ingredient is selected from a group consisting of butylidenephthalide, a pharmaceutically acceptable salt of butylidenephthalide, 2-pentanolybenzoic acid, a pharmaceutically acceptable salt of 2-pentanolybenzoic acid, and combinations thereof.

2. The method of claim 1, wherein the meningiomas are at least one of grade II atypical meningiomas, and grade III malignant meningiomas.

3. The method of claim 1, wherein the active ingredient is administered to the subject in an amount that is sufficient to kill meningioma cells and/or inhibit meningioma growth.

4. The method of claim 1, wherein the active ingredient is administered to the subject by one or more of the following administration routes: oral administration, subcutaneous injection, intramuscular injection, and inter-tissue implantation.

5. The method of claim 1, wherein the active ingredient is administered to the subject in a form of a wafer, wherein the wafer is implanted into the cavity generated by resecting meningioma to reduce the recurrence rate and prolong the progression-free survival of meningioma.

6. The method of claim 1, further comprising giving the subject a therapy selected from the following group: chemotherapy, radiotherapy, surgery, and combinations thereof.

7. The method of claim 6, wherein the chemotherapy comprises using an alkylating agent and/or an antimetabolite.

8. The method of claim 1, further comprising giving the subject a chemotherapy, wherein the chemotherapy comprises using an alkylating agent and/or an antimetabolite, and the alkylating agent and/or the antimetabolite is administered with the active ingredient simultaneously or separately.

9. A method for reducing meningioma recurrence rate, comprising administering to a subject in need thereof an effective amount of an active ingredient in a form of a wafer into the cavity generated by resecting meningioma, wherein the active ingredient is selected from a group consisting of butylidenephthalide, a pharmaceutically acceptable salt of butylidenephthalide, 2-pentanolybenzoic acid, a pharmaceutically acceptable salt of 2-pentanolybenzoic acid, and combinations thereof.

10. The method of claim 9, wherein the meningiomas are at least one of grade II atypical meningiomas, and grade III malignant meningiomas.

11. The method of claim 9, wherein the active ingredient is administered to the subject in an amount that is sufficient to inhibit meningioma growth.

12. The method of claim 9, wherein the active ingredient is administered to the subject by one or more of the following administration routes: oral administration, subcutaneous injection, intramuscular injection, and inter-tissue implantation.

13. The method of claim 9, wherein the active ingredient is administered to the subject in a form of a wafer, wherein the wafer is implanted into the cavity generated by resecting meningioma to reduce the recurrence rate and prolong the progression-free survival of meningioma.

14. The method of claim 9, wherein the subject has finished a therapy selected from the following group: chemotherapy, radiotherapy, surgery, and combinations thereof.

15. The method of claim 9, further comprising giving the subject a chemotherapy.

16. The method of claim 15, wherein the chemotherapy comprises using an alkylating agent.

17. The method of claim 9, further comprising giving the subject a chemotherapy, wherein the chemotherapy comprises using an alkylating agent, and the alkylating agent is administered with the active ingredient simultaneously or separately.

18. The method of claim 1, wherein when the method further comprises giving the subject temozolomide, the active ingredient is selected from a group consisting of 2-pentanolybenzoic acid, a pharmaceutically acceptable salt of 2-pentanolybenzoic acid, and combinations thereof.

* * * * *